(12) United States Patent
Kreitenberg et al.

(10) Patent No.: US 11,007,290 B2
(45) Date of Patent: May 18, 2021

(54) FLYING SANITATION DEVICE AND METHOD FOR THE ENVIRONMENT

(71) Applicant: DIMER, LLC, Los Angeles, CA (US)

(72) Inventors: Arthur Kreitenberg, Los Angeles, CA (US); Elliot M. Kreitenberg, Los Angeles, CA (US)

(73) Assignee: DIMER, LLC, Los Angeles, CA (US)

( * ) Notice: Subject to any disclaimer, the term of this patent is extended or adjusted under 35 U.S.C. 154(b) by 79 days.

(21) Appl. No.: 16/232,343

(22) Filed: Dec. 26, 2018

(65) Prior Publication Data

US 2019/0216958 A1    Jul. 18, 2019

Related U.S. Application Data

(60) Provisional application No. 62/618,948, filed on Jan. 18, 2018.

(51) Int. Cl.
| | |
|---|---|
| *A61L 2/10* | (2006.01) |
| *A61L 2/24* | (2006.01) |
| *B64C 39/02* | (2006.01) |
| *A61L 9/20* | (2006.01) |
| *B08B 7/00* | (2006.01) |

(52) U.S. Cl.
CPC .................. *A61L 2/10* (2013.01); *A61L 2/24* (2013.01); *A61L 9/20* (2013.01); *B64C 39/024* (2013.01); *A61L 2202/11* (2013.01); *A61L 2202/14* (2013.01); *A61L 2202/16* (2013.01); *A61L 2209/111* (2013.01); *B08B 7/0057* (2013.01); *B64C 2201/12* (2013.01); *B64C 2201/141* (2013.01)

(58) Field of Classification Search
CPC ............ A61L 2/10; A61L 2/24; B64C 39/024
See application file for complete search history.

(56) References Cited

U.S. PATENT DOCUMENTS

| | | | |
|---|---|---|---|
| 5,338,169 | A | 8/1994 | Buckley |
| 5,369,892 | A | 12/1994 | Dhaemers |
| 5,673,918 | A | 10/1997 | Bigari |
| 5,959,423 | A | 9/1999 | Nakanishi et al. |
| 6,311,974 | B1 | 11/2001 | Koga |
| 6,370,453 | B2 | 4/2002 | Sommer |
| 6,389,639 | B1 | 5/2002 | Worsham |
| 6,419,190 | B1 | 7/2002 | Nguegang |
| 6,565,668 | B1 | 5/2003 | Sandberg et al. |
| 6,779,714 | B2 | 5/2004 | Webb |
| 6,787,782 | B1 | 9/2004 | Krosney et al. |

(Continued)

FOREIGN PATENT DOCUMENTS

| | | |
|---|---|---|
| CN | 2621044 Y | 6/2004 |
| CN | 101756678 | 6/2010 |

(Continued)

*Primary Examiner* — Sean E Conley
(74) *Attorney, Agent, or Firm* — Greenberg Traurig, LLP

(57) ABSTRACT

A rover device for sanitizing spacecraft that emits germicidal ultraviolet light with means for sensing and directing rover location, orientation, velocity, trajectory and path is disclosed. Rather, the disclosed embodiment is a rover that uses propellers more in the fashion of a thruster on a satellite which uses short bursts to control satellite position in three translational planes and three rotational axes. Unlike a thruster, the propeller can be reversed, allowing motion in either direction.

8 Claims, 11 Drawing Sheets

(56) References Cited

U.S. PATENT DOCUMENTS

| | | |
|---|---|---|
| 6,889,449 B2 | 5/2005 | Silver |
| 6,992,301 B2 | 1/2006 | Fenc |
| 7,204,208 B2 | 4/2007 | Johnson et al. |
| 7,459,694 B2 | 12/2008 | Scheir et al. |
| 7,462,849 B2 | 12/2008 | Ferres et al. |
| 7,523,692 B1 | 4/2009 | Burns |
| 8,029,739 B2 | 10/2011 | Field et al. |
| 8,105,532 B2 | 1/2012 | Harmon et al. |
| 8,193,515 B2 | 6/2012 | Kreitenberg |
| 8,226,887 B2 | 7/2012 | Harmon et al. |
| 8,330,121 B2 | 12/2012 | Douglas |
| 8,999,238 B2 | 4/2015 | Kreitenberg |
| 9,144,618 B2 | 9/2015 | Kreitenberg |
| 9,840,339 B1* | 12/2017 | O'Brien ................. B64D 47/02 |
| 10,011,353 B1* | 7/2018 | Beckman ............. G05D 1/0858 |
| 10,159,761 B2 | 12/2018 | Kreitenberg |
| 2004/0056201 A1 | 3/2004 | Fink et al. |
| 2004/0244138 A1 | 12/2004 | Taylor et al. |
| 2005/0022844 A1 | 2/2005 | Field et al. |
| 2005/0159275 A1 | 7/2005 | Bullman et al. |
| 2006/0216193 A1 | 9/2006 | Johnson et al. |
| 2007/0158499 A1 | 7/2007 | Whittingham |
| 2008/0056933 A1 | 3/2008 | Moore et al. |
| 2008/0184518 A1 | 8/2008 | Taylor et al. |
| 2009/0193676 A1 | 8/2009 | Shengguang et al. |
| 2010/0028201 A1 | 2/2010 | Neister |
| 2011/0082668 A1 | 4/2011 | Escrig et al. |
| 2011/0167574 A1 | 7/2011 | Stout et al. |
| 2011/0256019 A1 | 10/2011 | Gruen et al. |
| 2012/0221192 A1 | 8/2012 | Seibt |
| 2012/0223216 A1 | 9/2012 | Flaherty et al. |
| 2012/0273340 A1* | 11/2012 | Felix .................... B01D 53/007 |
| | | 204/157.3 |
| 2013/0000675 A1 | 1/2013 | Hong et al. |
| 2013/0270459 A1 | 10/2013 | Fontani |
| 2014/0044590 A1 | 2/2014 | Trapani |
| 2014/0059796 A1 | 3/2014 | Boodaghians et al. |
| 2014/0241941 A1 | 8/2014 | Kreitenberg |
| 2016/0351089 A1* | 12/2016 | Salem ....................... B64B 1/58 |
| 2016/0375166 A1 | 12/2016 | Kreitenberg |
| 2017/0321877 A1* | 11/2017 | Polidoro ................. F24F 13/28 |
| 2018/0343847 A1* | 12/2018 | Ervin .................... A01M 1/226 |

FOREIGN PATENT DOCUMENTS

| | | |
|---|---|---|
| CN | 105944127 A | 9/2016 |
| DE | 3937706 | 5/1991 |
| GB | 2391799 | 2/2004 |
| JP | 63-135646 | 9/1988 |
| JP | H1057614 | 3/1998 |
| JP | 2000-325059 | 11/2000 |
| JP | 2005013723 | 1/2005 |
| JP | 2007/082747 | 4/2007 |
| JP | 2009/291349 | 12/2009 |
| JP | 2011/98156 | 5/2011 |
| WO | WO2008/010684 | 1/2008 |
| WO | WO2014/036217 | 3/2014 |

* cited by examiner

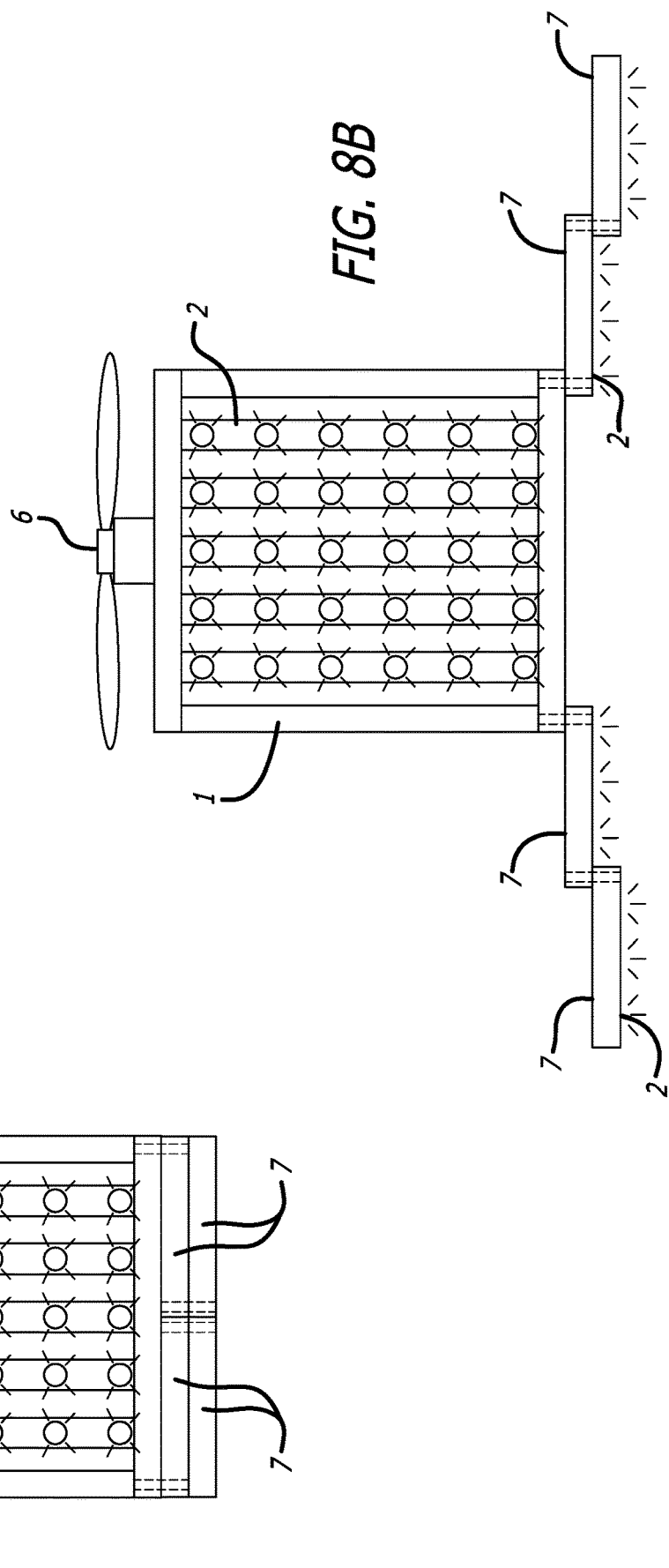

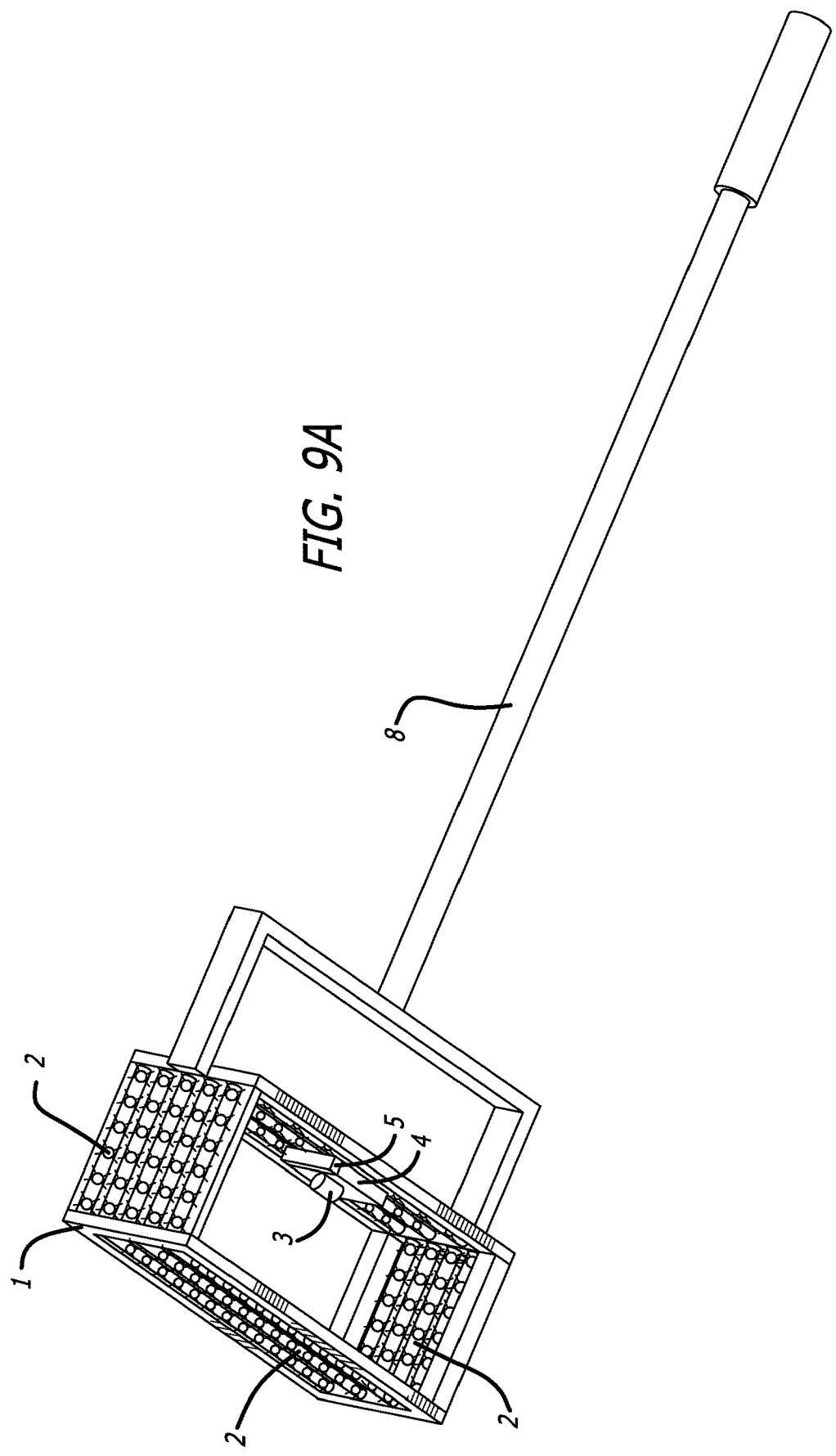

FLYING SANITATION DEVICE AND METHOD FOR THE ENVIRONMENT

RELATED APPLICATION

This application relates to and claims priority from 62/618,948 filed Jan. 18, 2018, entitled "A rover device for sanitizing spacecraft that emits germicidal ultraviolet light with means for sensing and directing rover location, orientation, velocity, trajectory and path", the content of which is incorporated by reference herein in its entirety.

BACKGROUND

The present disclosure relates to a flying device for effecting sanitation in the environment. The present disclosure is more particularly directed to a sanitation device that includes a source of ultraviolet (UV) radiation that is used to sanitize a surface, surrounding air and objects, including organic material. Additional disclosed embodiments of the present disclosure are directed to methods of sanitizing surfaces using the device. This disclosure further concerns sanitizing environments, particularly enclosed spaces.

SUMMARY

The present disclosure generally relates to a sanitation device for sanitizing surfaces, with a flying or hovering device and method such as for sanitizing spacecraft. The device emits germicidal ultraviolet light, and has means for sensing and directing the location, orientation, velocity, trajectory and path of a hovering, flying or rover device in the environment and in relation to surfaces.

In accordance with one disclosed embodiment of the disclosure, the sanitization device includes a mobile body and a source of UV radiation. The source of UV radiation is mounted to the mobile body, which is configured to travel over a surface. The source of UV radiation is configured to direct UV radiation to the surface at a dosage sufficient to diminish microbial loads to desired levels.

DRAWINGS

FIGS. 8A to 8C are different views of a fourth form of the device with arms which are extendible from a body and foldable in towards a body. As shown in FIG. 8C, the device is floating in a space station with its arms extended from the body.

Figure 1:
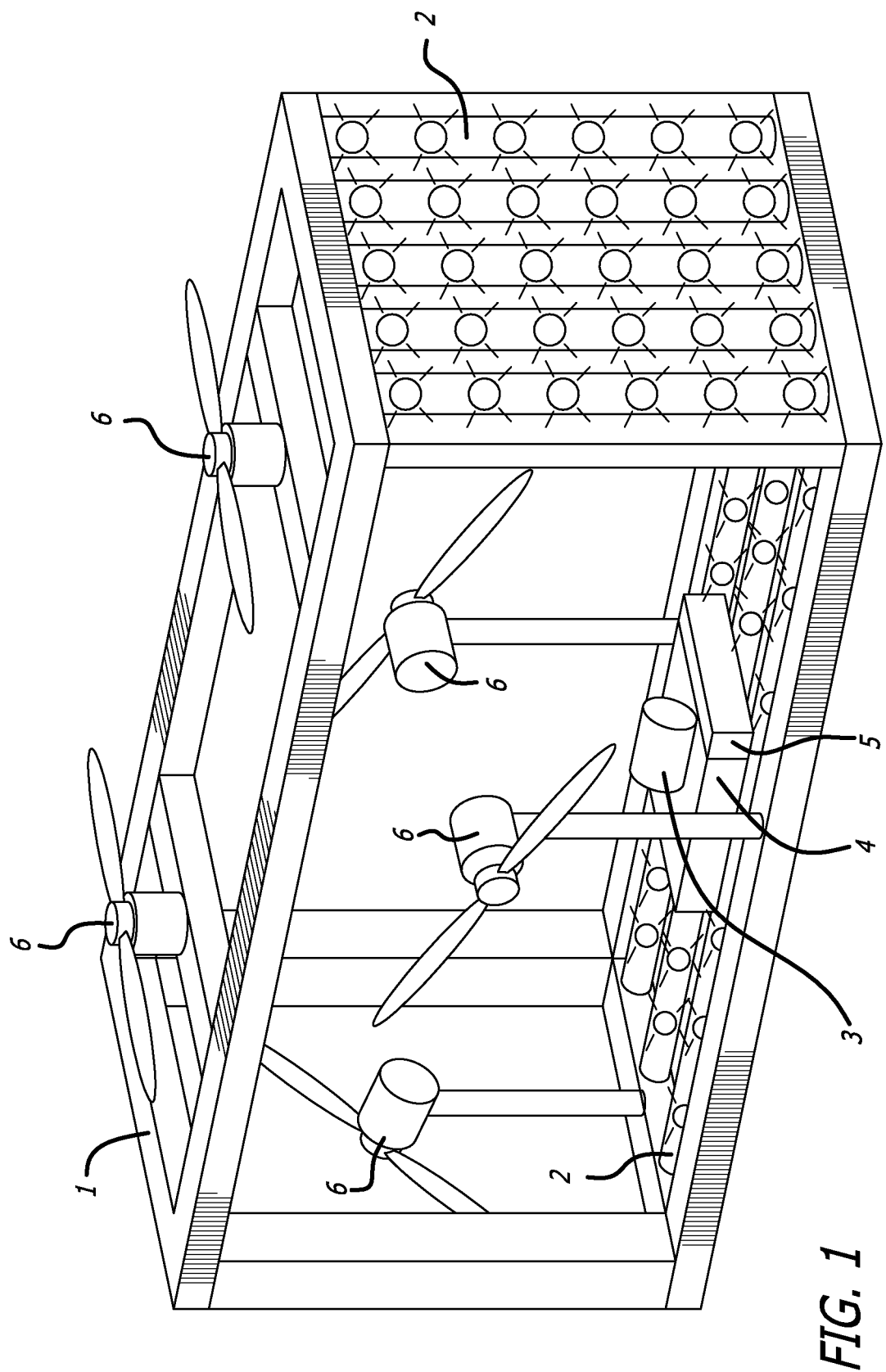
FIG. 1 is a perspective view of one form of the device.
Figure 2:
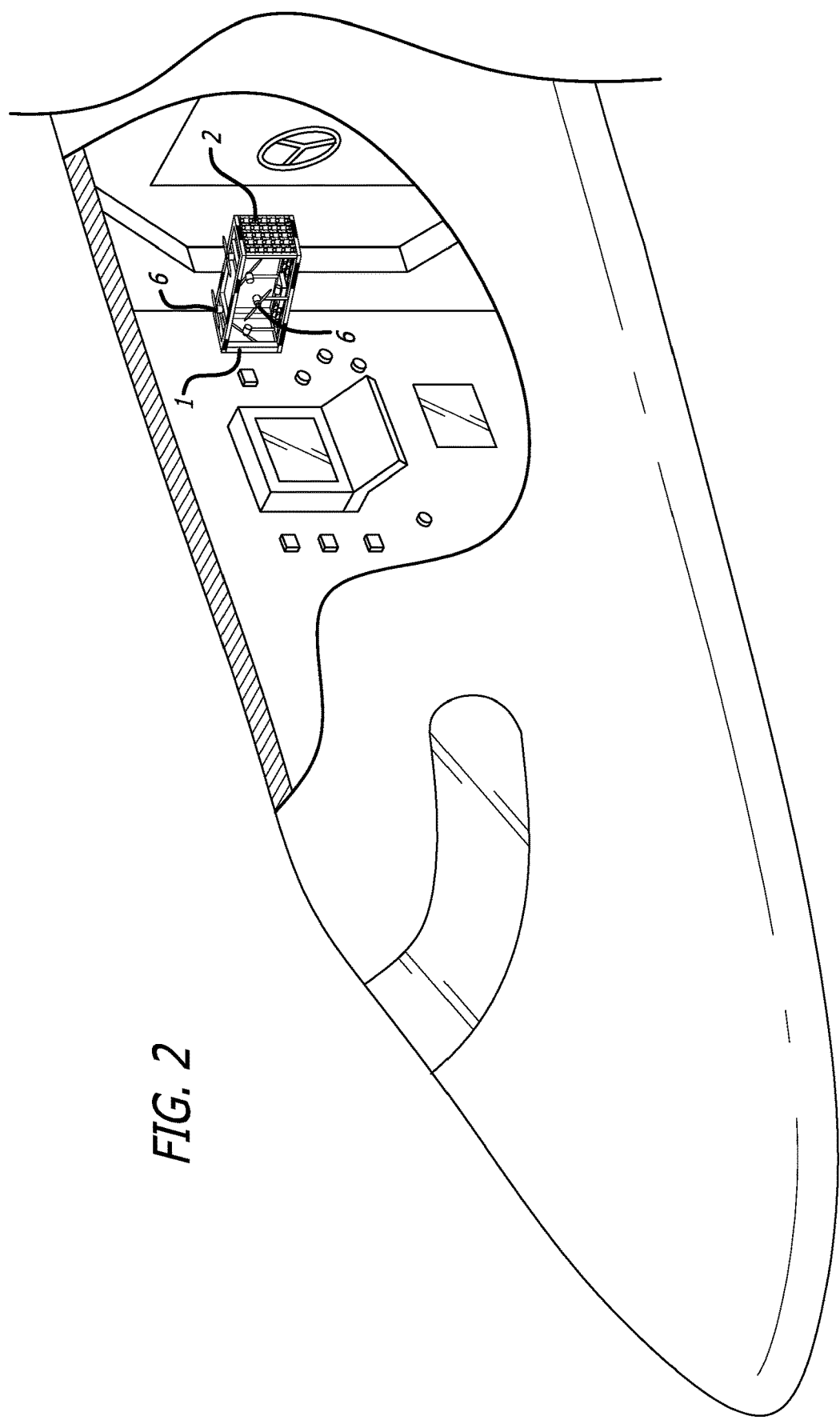
FIG. 2 is a perspective view of one form of the device in a space ship environment.
Figure 3:
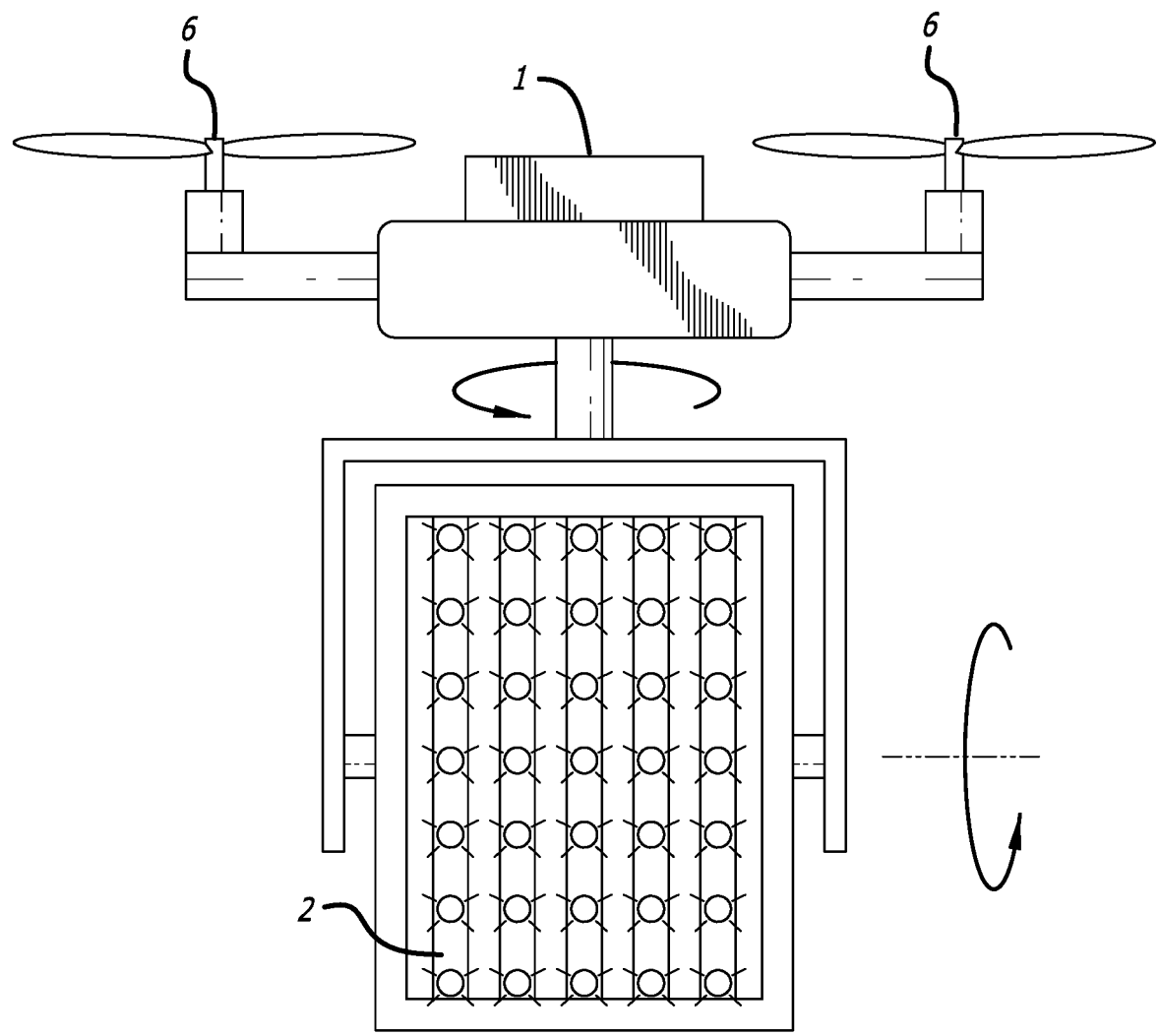
FIG. 3 is a front view of a second form of the device.
Figure 4:
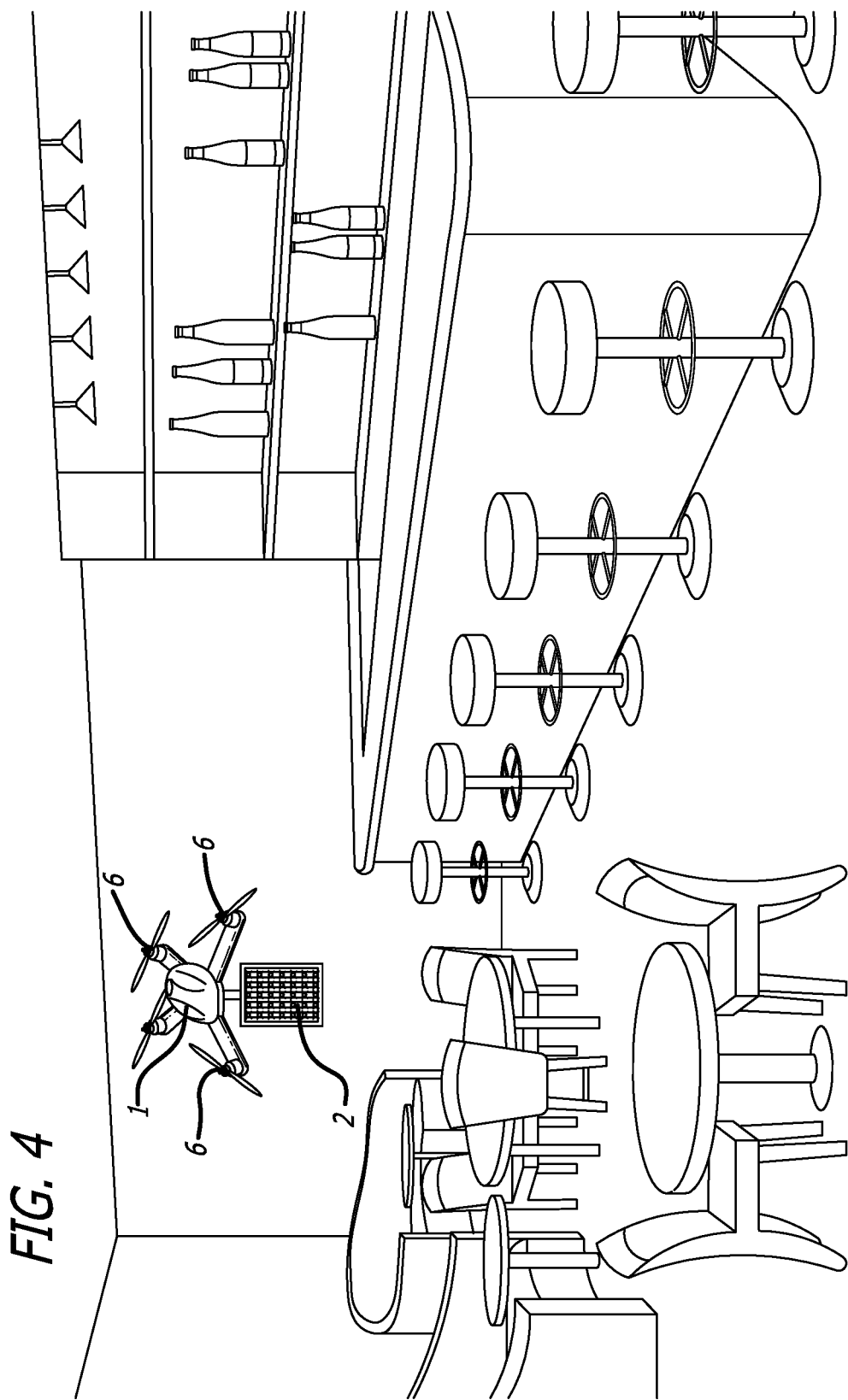
FIG. 4 is a perspective view of the second form of the device in a restaurant environment.
Figure 5:
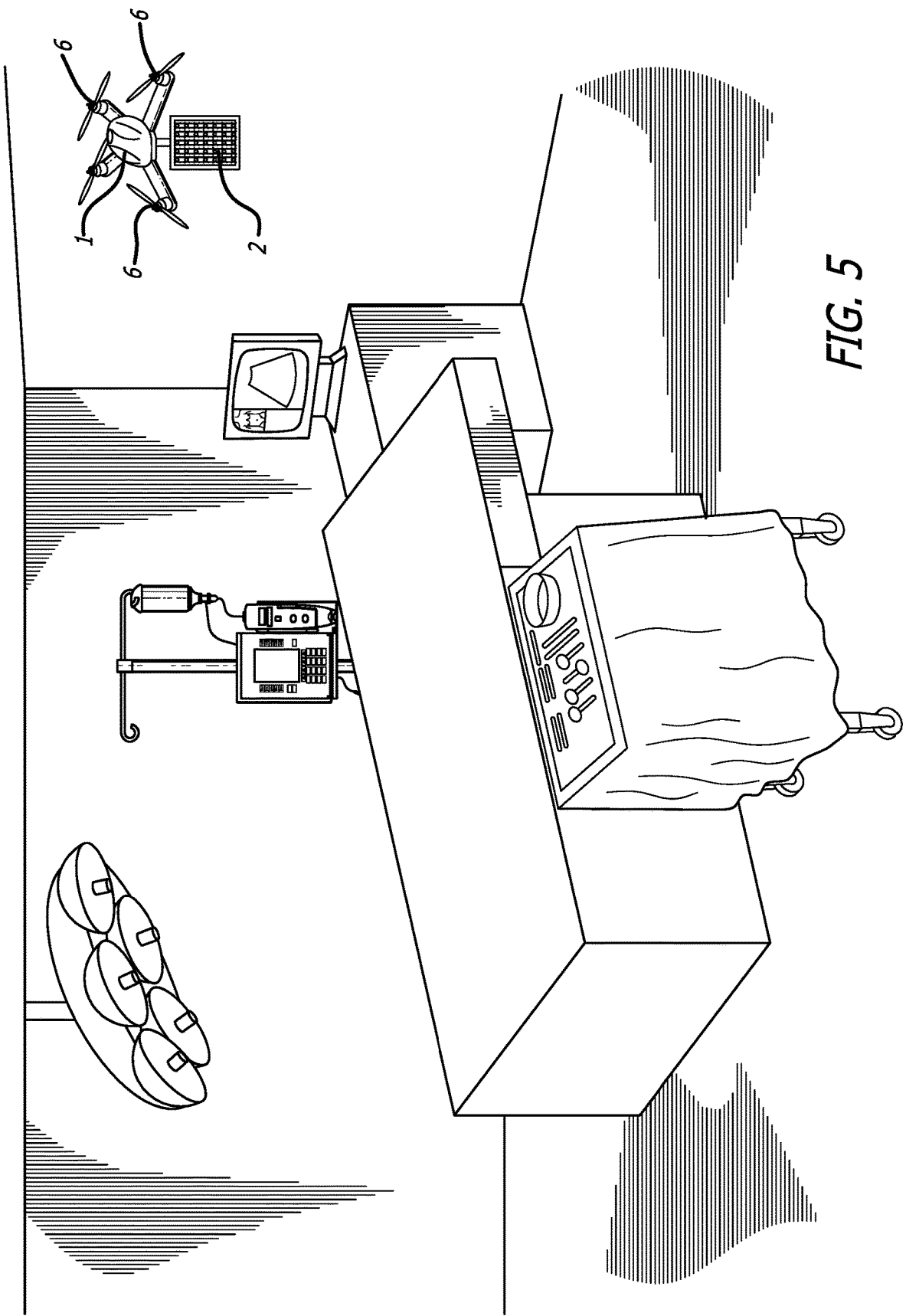
FIG. 5 is a perspective view of the second form of the device in a surgery room environment.
Figure 6:
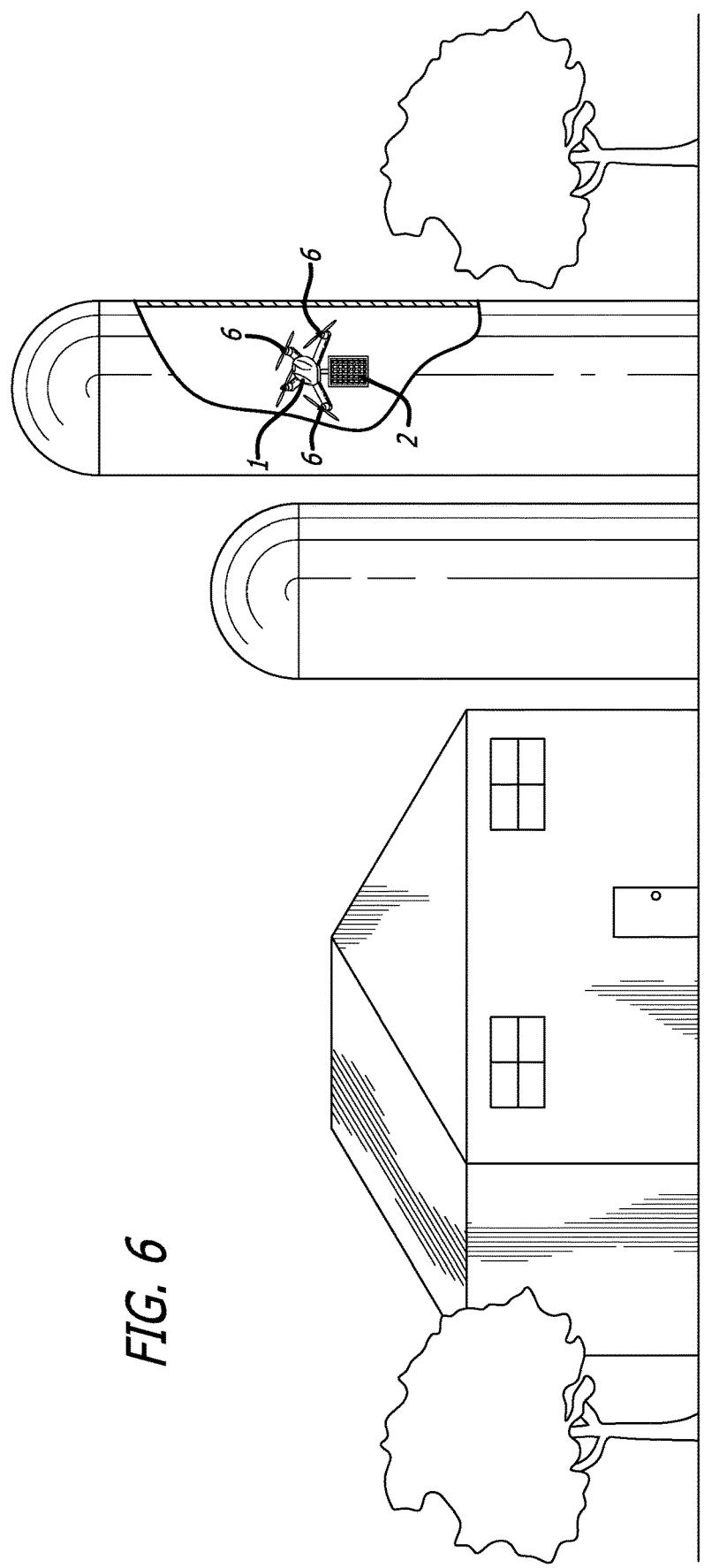
FIG. 6 is a perspective view of the second form of the device in a grain elevator industrial or farming environment.
Figure 7:
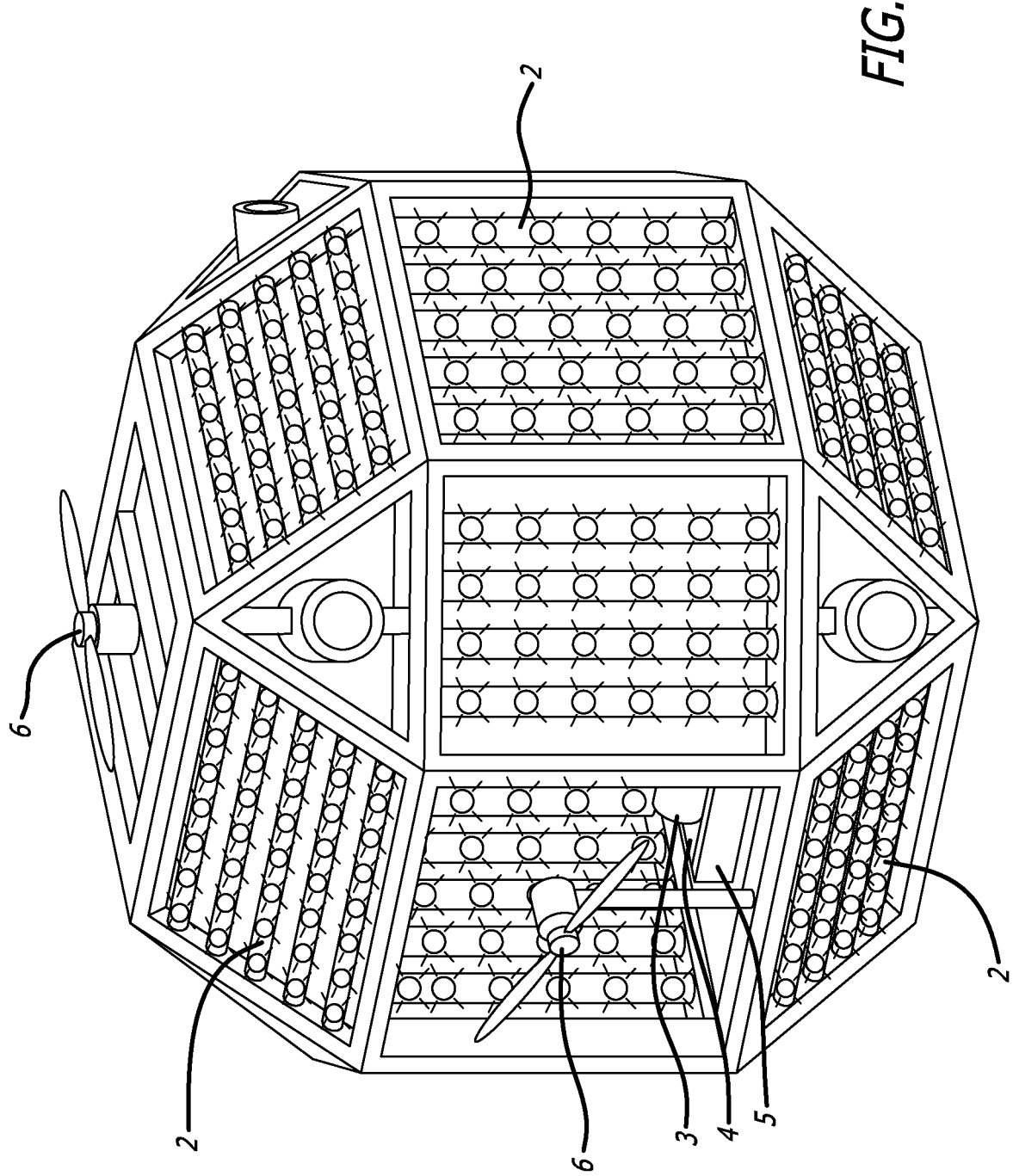
FIG. 7 is a view of a third form of the device, in s non-orthogonal shaped format.
Figure 8C:
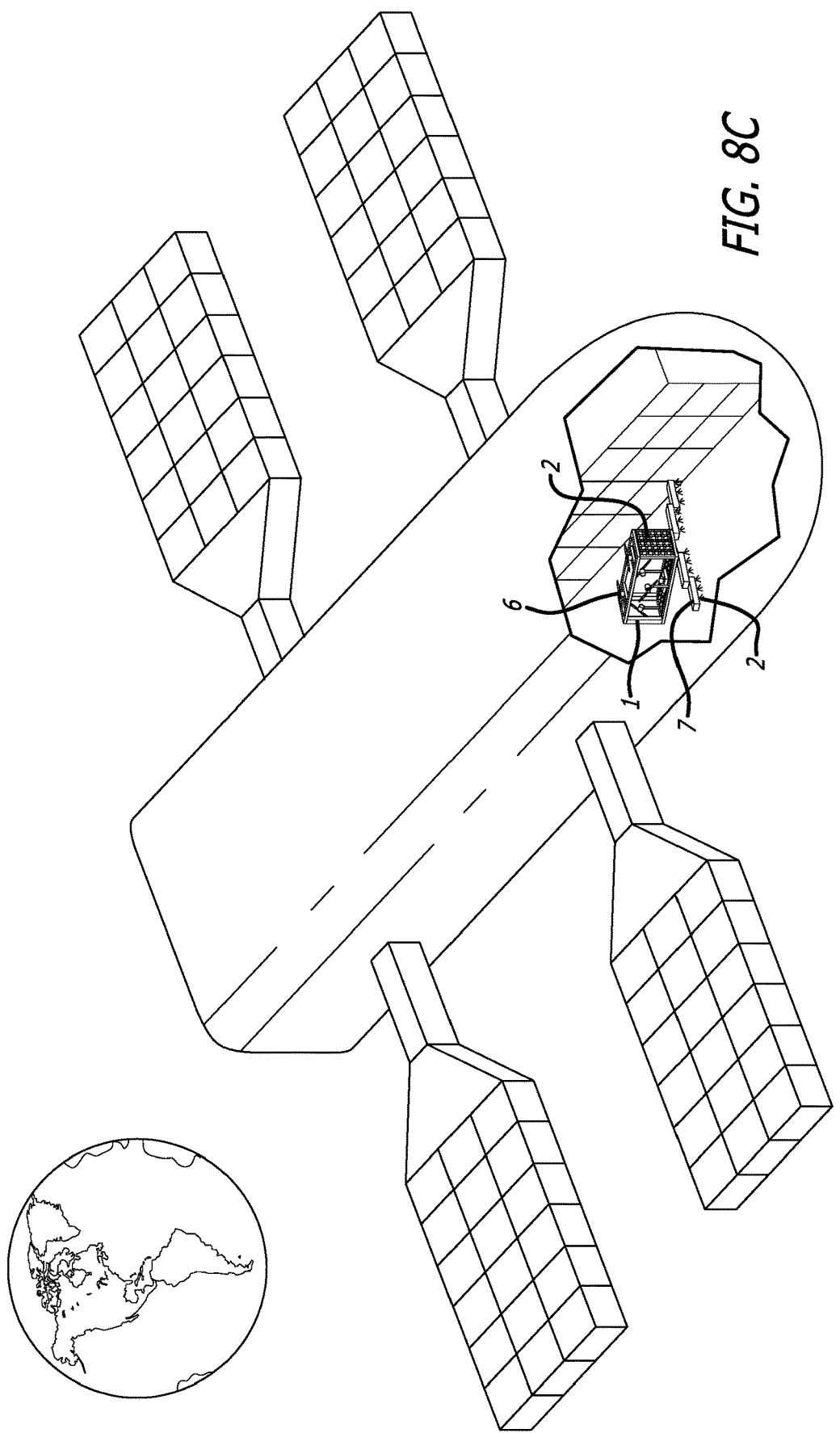
Figure 9B:
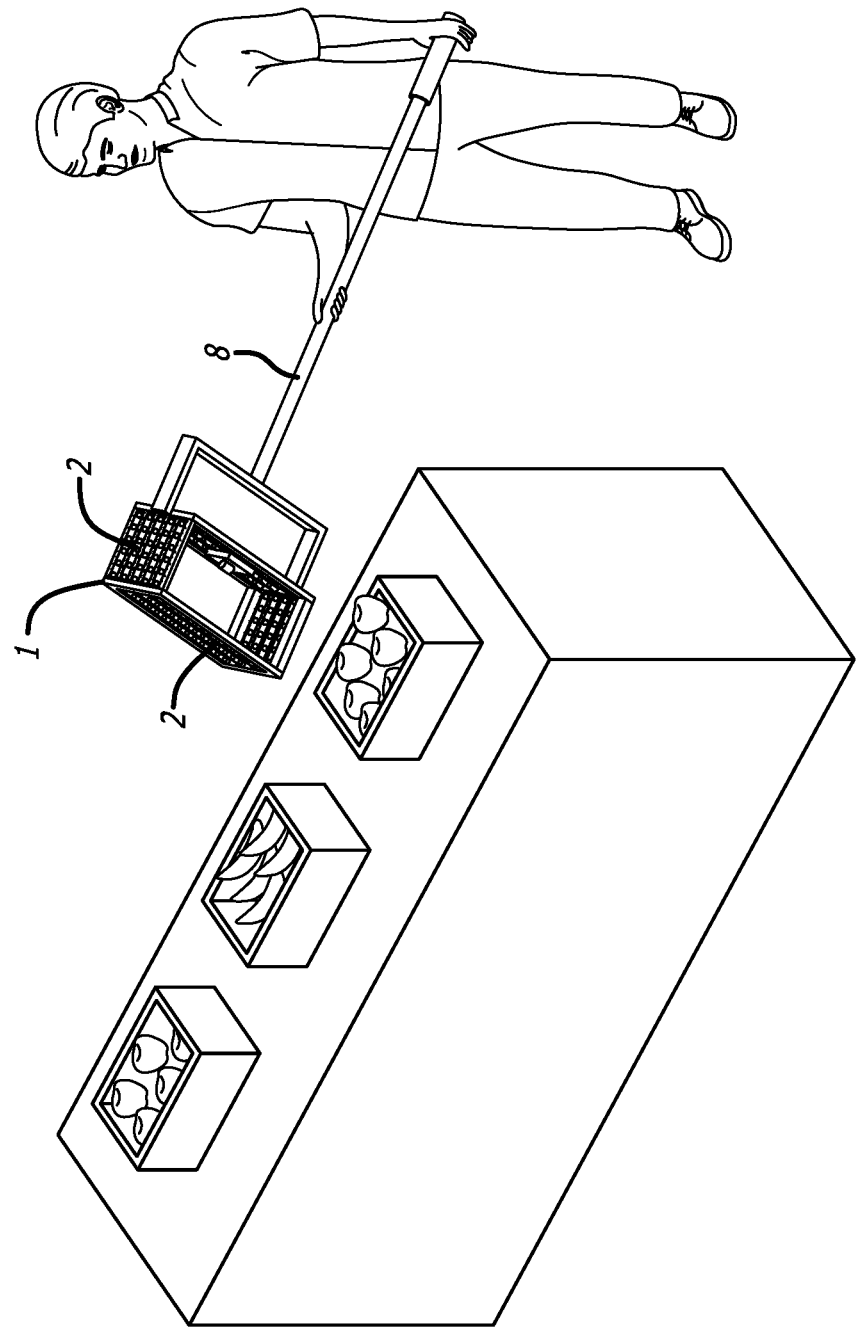

FIGS. 9A and 9B show the device at the end of a handle and as such the hand-held device can be maneuvered and used for instance in a non-fly mode. In FIG. 9B it is shown being used over organic material such as growing plants. Such use can be terrestrial or in space.

DETAILED DESCRIPTION

A sanitization device for sanitizing a surface inside a defined environment having structural elements with a surface comprises a mobile body configured to travel towards and about a surface of the structural elements. There is a source of UV radiation mounted to the mobile body and configured to direct UV radiation to the surface at a predetermined dosage. The mobile body includes a power source for propelling and suspending the device in space in the environment defined by the surface of the structure and negotiating movement of the device in the space defined by the surface of the structure. There is a power source for activating the UV radiation as the device moves in the environment.

The body includes one or more rotational propellers, and a motor for causing rotation of the propeller for imparting a propulsion of the body in direction caused by rotation of the propeller. There can be multiple rotational propellers, a motor for causing rotation of the propellers for imparting a propulsion of the body in different relative directions. This can be used by the degree of activation and rotation of the propellers, the propellers being selectively reversible. Each propeller can be mounted to direct propulsion in a different orthogonal direction relative the other propeller, the propellers being selectively reversible.

There can be multiple UV sources, each source being for directing radiation in a different direction, selectively in a different orthogonal direction relative to other sources. Each source can be for directing radiation in a different direction, selectively in a different orthogonal direction relative to other sources. There are control electronics for regulating the power to the propellers and UV sources.

The device can be for flying and hovering in the environment, the environment being a space located areas with substantially zero gravity, or as a drone in the environment, the environment being a terrestrial located structure.

There can be a motor for the mobile body and wherein the mobile body is steerable for negotiating the space in a space ship. In other cases, there is a motor for the mobile body so that the mobile body is steerable for negotiating the space in an enclosed building environment terrestrially located.

The disclosure includes a sanitization device for sanitizing a surface inside a defined environment having structural elements with a surface. There is a mobile body configured to travel towards and about a surface of the structural elements, and a source of UV radiation mounted to the mobile body and configured to direct UV radiation to the surface at a predetermined dosage. The mobile body includes a power source for propelling and suspending the device in space in the environment defined by the surface of the structure and negotiating movement of the device in the space defined by the surface of the structure. There is a power source for activating the UV radiation as the device moves in the environment.

The body includes one or more rotational propellers, a motor for causing rotation of the propeller for imparting a propulsion of the body in direction caused by rotation of the propeller. The body includes multiple rotational propellers, a motor for causing rotation of the propellers for imparting a propulsion of the body in a different relative direction as caused by the degree of activation and rotation of the propellers, the propellers being selectively reversible. Each propeller is mounted to direct propulsion in a different orthogonal direction relative the other propeller.

The body includes multiple UV sources, each source being for directing radiation in a different direction, selectively in a different orthogonal direction relative to other sources.

The device includes control electronics for regulating the power to the propellers and UV sources.

In some cases, the device is for flying and hovering in the environment, the environment being a space located areas with substantially zero gravity. There is a motor for the mobile body and wherein the mobile body is steerable for negotiating the space in a space ship.

In other cases, the device is for flying as a drone in the environment, the environment being a terrestrial located structure. The device includes a motor for the mobile body and wherein the mobile body is steerable for negotiating the space in an enclosed building environment terrestrially located.

Spacecraft harbor and transport microorganisms that can cause undesired contamination. These bacteria, viruses, fungi, and mold may cause human disease, damage the spacecraft and potentially cross contaminate worlds. It is therefore desirable to diminish or eliminate this bioburden.

Although UVC has been utilized for earth-based applications in both stationary and mobile platforms, none anticipate the microgravity of spaceflight.

Rather, the disclosed embodiment of the current disclosure is a rover that uses propellers more in the fashion of a thruster on a satellite which uses short bursts to control satellite position in three translational planes and three rotational axes. Unlike a thruster, the propeller can be reversed, allowing motion in either direction.

In one version of the disclosure as discussed here there is: a 1) Frame; 2) UVC sources; 3) Battery; 4) Sensor package; 5) Microprocessor/microcontroller; and 6) Propellers/Motors.

The device can have having extendible and foldable arms 7 with the mobile body. The arms mount at least one source of UV radiation.

In some cases, there is a handle 8 for the mobile body and wherein the mobile body is steerable manually for negotiating the space.

The frame 1 is the structure to which the other components attach. The frame 1 may of any shape and size suitable for the intended purpose. In one disclosed embodiment, the frame 1 is a rectangular prism. Other shapes of frame are possible, for instance, spherical, polyhedral, ovoid or cylindrical in part or in whole.

The UVC sources 2 may be clustered in arrays and attach onto at least one surface of the frame 1 in a manner to direct the UVC away from the frame 1. In the disclosed embodiment, the UVC sources are LEDs and located on 2 orthogonal surfaces. The UVC sources 2 are controlled by the microprocessor/microcontroller 5 and powered only when near the target spacecraft surface intended to be sanitized. Only those UVC sources 2 that are relevant to the spacecraft surface need be powered. Other arrangements of arrays are possible, for instance, spherical or cylindrical surfaces in part or whole and covering more or less of the 360 degree, 3-dimensional spherical scope or span, extending beyond the frame, variably extensible, telescoping, folding, and rolling.

The battery 3 is of a form factor and location having minimum impact on air flow through the frame 1 and disrupting center of mass. The battery has sufficient power output and capacity to handle the assigned disinfection task. The battery 3 powers the propellers 6, the microprocessor/microcontroller 5, and the payload, in this instance the UVC sources, 2. In microgravity, the "weight" of the battery is undefined but less mass is to more easily control navigation of the rover. The disclosed embodiment utilizes a rechargeable battery. The battery may be swappable.

The sensor package 4 may contain proximity sensors, gyroscopes and other positional sensors capable of determining the rover position, orientation, trajectory and velocity relative to the spacecraft interior. Sensors are gravity independent. Sensing may be supplemented by location markers affixed to one or more points within the spacecraft. The rover can have a self-contained attitude stabilization mechanism, known in the art of satellites. The disclosed embodiment is an internal gyroscope, although rotation of the rover, about an axis perpendicular to the UVC source 2 can provide attitude stabilization without compromising UVC exposure of spacecraft surfaces. The microprocessor/microcontroller 5 may be located anywhere on the frame 1 to permit maximal airflow. The microprocessor/microcontroller 5 accepts data from the sensor package 4 to determine the rover position, orientation and velocity relative to the spacecraft interior. The microprocessor/microcontroller also receives data from UVC meters located on the spacecraft interior to ensure target UVC exposure dosing. The microprocessor/microcontroller 5 may be pre-programmed with the task. The microprocessor/microcontroller also has collision avoidance capability using the propellers 6, in case an unanticipated object is encountered. Finally, the microprocessor/microcontroller 5 directs the propellers 6 to achieve desired position, orientation, velocity, trajectory and path.

Motor driven propellers 6, at a plurality of locations and orientations are attached to frame 1. In an alternative disclosed embodiment, a single propeller 6 may be attached to a gimbal type mechanism to allow propulsion in multiple directions. Similarly, variable deflectors may be used to direct airflow off the propellers 6 to vary the rover position, orientation, velocity, trajectory and path. The propellers may be powered to rotate in either direction. The propellers are powered by the battery 3 and controlled by the microprocessor/microcontroller 5.

Another disclosed embodiment of the disclosure could also be used outside the spacecraft. Rather than using propellers 6, compressed gas ejected via thrusters analogous to any satellite or spacecraft could be used to determine rover position and path.

The rover may also utilize a docking port to mate with a separate docking station located on the spacecraft. The docking station serves as a home base for battery 3 recharging and communicates with the rover to help determine rover position, orientation, velocity, trajectory and path. The docking station is wired to the spacecraft electrical system. Docking may be aided by magnetic attraction.

The device works by having the rover is programmed to regularly sanitize the spacecraft interior, for example at 24-hour intervals. A plurality of rovers may be utilized for multi-compartment spacecraft such as International Space Station, assigning at least one rover per module. It is recommended that disinfection be scheduled at a time when the compartment is unoccupied.

The rover departs from the docking station with a preferably fully charged battery. The path of the rover is determined by the specific surfaces to be sanitized. It may be optimal to choose a predetermined path specific to a compartment. Alternatively, a "Simultaneous Localization and Mapping" (SLAM) protocol may be employed to learn the specific three-dimensional module topography, or a random path may be optimal.

The rover hovers over the surface. The UVC sources 2 are powered to expose the target surface. In the disclosed embodiment, there are 2 orthogonally arranged arrays of UVC sources, one larger and one smaller, depending on the surface to be sanitized. The smaller array allows the rover to enter voids the size of a human hand for sanitization. This orthogonal arrangement also allows more efficient sanitization of a corner.

The total light energy delivered to a surface, typically measured in Joules per unit area, is determined by the amount of time, and/or speed of travel, the rover is over the surface. Additionally, the light energy intensity, typically measured in Watts per unit area, may be varied by the microprocessor/microcontroller 5, analogous to a dimmer control.

Doses are known for various target pathogens so the energy may vary depending on the target microbe. UVC meters may be located on the spacecraft interior to measure delivered dose. The UVC sensors may communicate with the rover microprocessor/microcontroller 5 to provide input. The propellers 6 are selectively powered, in forward or reverse via the microprocessor/microcontroller 5 in a manner to achieve the desired UVC exposure level at all target surfaces. Only very brief intervals of propeller 6 motions are required to initiate translation or rotation and a very brief reversal of propeller rotation is required to bring the rover to rest. As such, the vast majority of battery 3 power is utilized for powering the UVC sources 2. In an alternative disclosed embodiment, gas emitting thrusters may be used rather than propellers.

Reverse pitch propellers can be utilized to counteract any rotational moment created by 2 propellers spinning in the same direction.

Once the rover has completed its assigned task, it returns to the base station for recharging. The rover may also be programmed for sequential sanitization, for example, first one half of a compartment followed by the second half after a fresh battery charge.

These are known hardware, mechanisms and algorithms for example, Simultaneous Localization and Mapping, Collision Avoidance, Proximity Sensing, Gyroscopic guidance.

The device is made by a frame made of lightweight strong material. The other various components are securely mounted to the frame to accomplish the desired effect. The components are powered by the battery.

All of the numbered components may be necessary. Any sort of additional components to accomplish the mission of the rover may be added. Additionally, a plurality of propellers may be used in various orientations to achieve a high degree of control of location and orientation of rover.

A reporting function may be useful to keep crews and ground support apprised of device function and activities to monitor sanitization of spacecraft.

The frame may be of any shape suitable and practical for the specific spacecraft and function. The propellers may be oriented in any configuration to allow complete command and control.

The optimal configuration for use of the disclosure requires little or no human interaction. Once the rover and base station are installed and programmed, the rover should function autonomously.

Additionally: The rover described has on-board germicidal UVC sources to disinfect surfaces. Additional features, such as a gathering of debris can be added.

While the device, apparatus and method have been described in terms of what are presently considered to be the most practical and disclosed embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all disclosed embodiments of the following claims.

What is claimed is:

1. A method of sanitizing a spacecraft with a sanitization device located in the spacecraft, located in a zero gravity environment, and inside a defined environment in the spacecraft, and the spacecraft having structural elements with a surface the method comprising the steps of:
   providing the sanitization device, the sanitization device comprising a mobile body configured to travel towards and about the surface of the structural elements, and a source of UV radiation mounted to the mobile body and configured to direct UV radiation to the surface at a predetermined dosage and sanitize the surface;
   the mobile body including a first power source for propelling and suspending the device in a space in the spacecraft wherein the mobile body is steerable for negotiating the space in the spacecraft, and in the environment defined by the surface of the structure and negotiating movement of the device in the space defined by the surface of the structure, and a second power source for activating the UV radiation source as the device moves in the zero gravity environment;
   control electronics for regulating the power to the propellers and UV source;
   the body including multiple rotational propellers, a motor for causing rotation of the propellers for imparting a propulsion of the body in different direction as caused by the degree of activation and rotation of the propellers, each propeller being mounted to direct propulsion in a different orthogonal direction relative the other propeller, the propellers being selectively reversible;
   a self-contained attitude stabilization mechanism operable in the zero gravity environment;
   configuring the mobile body to travel towards and about the surface of the structural elements,
   configuring the UV radiation to be directed to the surface at a predetermined dosage to sanitize the surface;
   propelling and suspending the device in the space in the spacecraft;
   steering the mobile body to negotiate the space in the spacecraft, and in the environment defined by the surface of the structure;
   negotiating movement of the device in the space defined by the surface of the structure;
   activating the second power source for the source of UV radiation as the device moves in the zero gravity environment;
   regulating through control electronics the power to the propellers and the UV source; and
   attitude stabilizing the device to be operable in the zero gravity environment.

2. The method of claim 1 including providing the device with extendible and foldable arms attached to the mobile body and wherein the arms include at least one additional source of UV radiation.

3. The method of claim 1 including a handle for carrying the mobile body and manually steering and negotiating through the space.

4. The method of claim 1 comprising: providing additional sources of UV radiation mounted in a non-orthogonal relationship relative to each other.

5. The method of claim 1 including operating the propellers in short bursts to control position in three translational planes and three rotational axes and reversing the propellers to allow motion in either direction.

6. The method of claim 1 including mating the mobile body in a docking port with a separate docking station located in the spacecraft in the zero gravity environment, the docking station being in the zero gravity environment serving as a base for battery recharging, determining device position, orientation, velocity, trajectory, and path; selectively wiring the docking station to a spacecraft electrical system; and selectively aiding docking by magnetic attraction.

7. The method of claim 1 including providing the device with proximity sensors and positional sensors for determining the mobile device position, orientation, trajectory and velocity relative to the spacecraft interior, the proximity and positional sensors being gravity independent, and being operable in the zero gravity environment.

8. The method of claim 1 including providing location marking with location markers affixed to one or more points within the spacecraft, and being operable in the zero gravity environment.

\* \* \* \* \*